US00PP12121P2

(12) United States Plant Patent
Zary

(10) Patent No.: US PP12,121 P2
(45) Date of Patent: Oct. 2, 2001

(54) GRANDIFLORA ROSE PLANT NAMED 'JACBRANT'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,970

(22) Filed: Dec. 6, 1999

(51) Int. Cl.[7] ..... A01H 5/00
(52) U.S. Cl. ..... Plt./137
(58) Field of Search ..... Plt./130, 137, 138

*Primary Examiner*—Howard J. Locker
(74) *Attorney, Agent, or Firm*—Klarquist Sparkman Campbell Leigh & Whinston, LLP

(57) ABSTRACT

A grandiflora rose plant having large flowers of novel coloration presented singly and in large, open clusters, tall, upright growth habit, glossy, dark green foliage, and good disease resistance.

1 Drawing Sheet

The present invention relates to a new and distinct variety of rose plant of the grandiflora class which was orginated by me by crossing the variety AROcad (U.S. Plant Pat. No. 5,168), with the variety JACient (U.S. Plant Pat. No. 6,725).

The primary objective of this breeding was to produce a new rose variety having the large flower size, tall, upright plant and broad petals of the female parent, combined with the glossy, dark green foliage, vigorous growth and excellent health of the male parent. The objective was substantially achieved, along with other desirable improvements, as evidenced by the following unique combination of characteristics that are outstanding in the new variety and that distinguish it from its parents, as well as from all other varieties of which I am aware:

1. Novel flower coloration;
2. Dark green, glossy foliage;
3. Good disease resistance;
4. Tall, upright growth habit; and
5. Flowers presented singly and in large, open clusters.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—AROcad (U.S. Plant Pat. No. 5,168).
*Pollen parent.*—JACient (U.S. Plant Pat. No. 6,725).
Classification:
*Botanical.*—*Rosa hybrida.*
*Commercial.*—Grandiflora.

FLOWER

Observations made from specimens grown in a garden environment at Somis, Calif. from March 1998 to August 1999.

Blooming habit: Continuous.
Bud:
*Size.*—About 1½ inches long when the petals start to unfurl.
*Form.*—The bud form is long; pointed ovoid.
*Color.*—When sepals first divide, bud color is close to Greyed-Red Group 180A. When half blown, the upper sides of the petals are Red Group 49D; and the lower sides of the petals are close to Red Group 51C, except near the petal base where the lower ¼ of the petal is close to Greyed-Red Group 180D.
*Sepals.*—Color: Green Group 138B except where exposed to bright sunlight. Then it is blushed with Greyed-Purple Group 184B. Surface texture: Covered in fine hairs. There are three lightly appendaged sepals. There are two unappendaged sepals with hairy edges.
*Receptacle.*—Color: Green Group 137D. Shape: Funnel. Size: Medium (about 5/16 inch×3/16 inch). Surface: Smooth.
*Peduncle.*—Length: Medium (about three inches). Surface: Prickly. Color: Greyed-Purple Group 184B. Strength: Stiff; erect.
Bloom:
*Size.*—Large. Average open size is four inches.
*Borne.*—Singly and several together in large, open, flat clusters of five to seven blooms.
*Stems.*—Strength: Strong. Average length is about 14 to 18 inches.
*Form.*—When first open: High centered. Permanence: Flattens; outer petals curl back.
*Petalage.*—Number of petals under normal conditions: 30 to 35.
*Color.*—The upper sides of the petals are Red Group 49D. The reverse sides of the petals are close to Red Group 51C except for the bottom ¼ of the petal, which is close to Greyed-Red Group 180D. The base of each petal has on the upper surface a ⅜ inch×¼ inch Yellow-Orange Group 21C color spot. The lower surface has a 3/16 inch×3/16 inch Yellow-Green Group 144D color spot. The major color on the upper side is Red Group 49D.
*Variegations.*—None.
*Discoloration.*—The general tonality at the end of the first day: No change. At the end of the third day: No change.

*Fragrance.*—Moderate; spicy.

Petals:

*Texture.*—Thick.

*Shape.*—Round.

*Form.*—Tips slightly recurved.

*Arrangement.*—Imbricated. No petaloids in the center.

*Persistence.*—Petals drop off cleanly before drying.

*Lastingness.*—On the plant: Long (about six or seven days). As a cut flower: Long (about seven or eight days).

Reproductive parts:

*Anthers.*—Size: Medium. Quantity: Many. Color: Yellow-Orange Group 21C. Arrangement: Regular around styles.

*Filaments.*—Color: Red Group 54B.

*Pollen.*—Present.

*Styles.*—Color: Red Group 53D.

*Stigmas.*—Color: Greyed-Yellow Group 161D.

Plant:

*Form.*—Bush.

*Growth.*—Vigorous; upright; branching. At maturity, height is five feet, width is four feet.

Foliage: Number of leaflets on normal mid-stem leaves: Five or seven.

*Size.*—Medium (5 inches long×3½ inches wide).

*Quantity.*—Normal.

*Color.*—New foliage: Upper and lower surfaces: Greyed-Purple Group 187B. Old foliage: Upper surface: Green Group 139A. Lower surface: Green Group 138A.

Leaflets:

*Shape.*—Pointed oval.

*Texture.*—Leathery; glossy.

*Edge.*—Serrated.

*Serration.*—Single; small.

*Petiole rachis.*—Color: Upper: Greyed-Purple Group 185A when young, then Green Group 137D. Lower: Green Group 138A.

*Petiole underside.*—Smooth; with occasional prickles.

*Stipules.*—Long (about ¾ inch); bearded; edged in glands.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked slightly downward.

*Color when young.*—Greyed-Purple Group 185C.

*Color when mature.*—Greyed-Orange Group 165D.

Small prickles:

*Quantity.*—On main stalks: Few, on the peduncles only. On laterals: Few, on the peduncles only.

*Color.*—Greyed-Purple Group 185C.

I claim:

1. A new and distinct variety of rose plant of the grandiflora class, substantially as herein shown and described, characterized particularly by its large flower of novel coloration presented singly and in large, open clusters, tall, upright growth habit, glossy, dark green foliage, and good disease resistance.

* * * * *

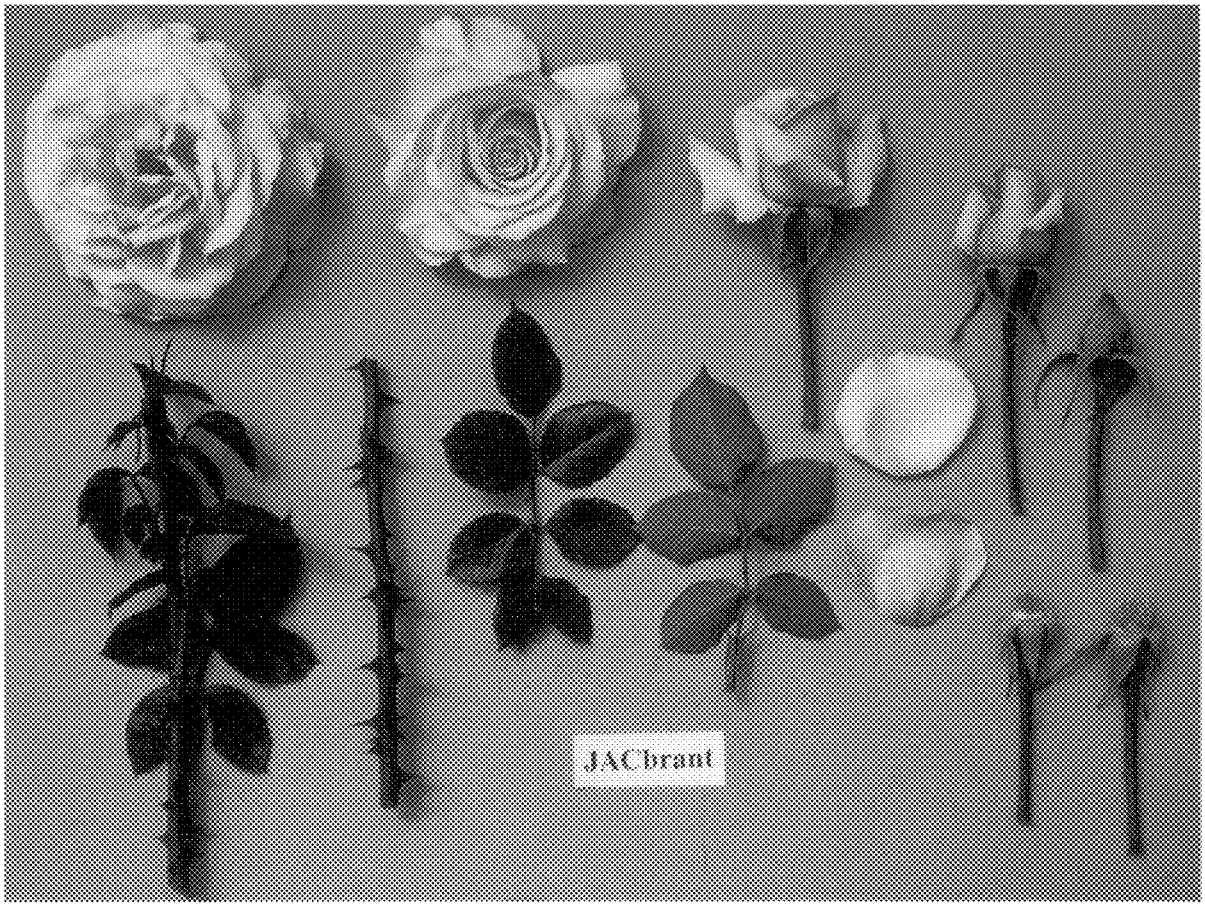
JACbrant